United States Patent [19]

Ikura et al.

[11] 4,208,411
[45] Jun. 17, 1980

[54] IMIDAZOLE DERIVATIVES HAVING FUNGICIDAL ACTIVITY

[75] Inventors: Katsuyata Ikura, Ninomiya; Kiyoshi Katsuura, Ohiso; Akira Nakada, Ohiso; Masami Mizuno, Oshio, all of Japan

[73] Assignee: Nippon Soda Company Limited, Tokyo, Japan

[21] Appl. No.: 886,558

[22] Filed: Mar. 14, 1978

[30] Foreign Application Priority Data

Jul. 27, 1977 [JP] Japan .................. 52-89940

[51] Int. Cl.² .............. A01N 9/22; C07D 233/56; C07F 1/08; C07F 3/06
[52] U.S. Cl. ............... 424/245; 424/273 R; 548/341; 548/103
[58] Field of Search .......... 260/299; 548/341; 424/273 R, 245

[56] References Cited

U.S. PATENT DOCUMENTS

| | | | |
|---|---|---|---|
| 3,993,469 | 11/1976 | Regel et al. ................. | 71/92 |
| 4,080,462 | 3/1978 | Brookes et al. .............. | 424/273 R |
| 4,085,209 | 4/1978 | Miller et al. ................. | 424/245 |

FOREIGN PATENT DOCUMENTS

| | | | |
|---|---|---|---|
| 52-39674 | 3/1977 | Japan ....................... | 548/341 |
| 52-46071 | 4/1977 | Japan ....................... | 548/341 |

*Primary Examiner*—Alton D. Rollins
*Assistant Examiner*—Diana G. Rivers
*Attorney, Agent, or Firm*—George B. Oujevolk

[57] ABSTRACT

Compounds of the general formula

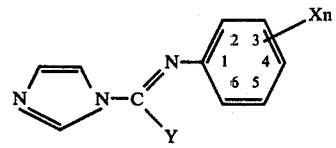

wherein
X is a same or different substituent which is halogen, lower alkyl, nitro or lower haloalkyl;
n is 1 or 2;
Y is alkoxyalkyl, lower alkenyloxyalkyl, phenoxyalkyl or substituted phenoxyalkyl;
or metal complexes of the compounds defined herein above.

The compounds are useful as fungicides.

9 Claims, No Drawings

IMIDAZOLE DERIVATIVES HAVING FUNGICIDAL ACTIVITY

DETAILED DESCRIPTION OF THE INVENTION

The present invention relates to a novel imidazole derivatives and metal complexes thereof, to a process for the preparation thereof and their uses as fungicides, in particular to a fungicidally active composition and method for controlling fungi.

It is disclosed in the Japanese published unexamined patent application No. 39674/77 that some imidazole derivatives have fungicidal activity. The imidazole derivatives are indicated by the general formula

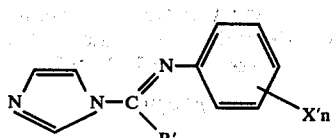

wherein R' is alkyl, X' is halogen, nitro, lower alkyl or lower alkoxy, and n is 0, 1 or 2.

It is also disclosed in the Japanese published unexamined patent application No. 46071/77 that some other imidazole derivatives have fungicidal activity. Those imidazole derivatives are shown by the general formula

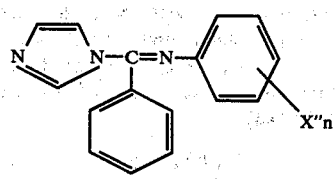

wherein X" is methyl, chlorine, bromine, nitro or trifluoromethyl, and n is 1 or 2.

Although these known imidazole derivatives have fungicidal activity, the activity is not sufficient and they cause phyto-toxicity to plants. Therefore these known compounds can not be put to practical use as fungicides.

It has been found that imidazole derivatives of the general formula

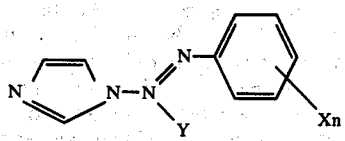

wherein
X is a same or different substituent which is halogen, lower alkyl, nitro or lower haloalkyl;
n is 1 or 2;
Y is alkoxyalkyl, lower alkenyloxyalkyl, phenoxyalkyl or substituted substituted phenoxyalkyl;
and metal complexes of the said imidazole derivatives have outstanding fungicidal activity and cause no phyto-toxicity to plants.

Preferable compounds as fungicides are the compounds of the general formula

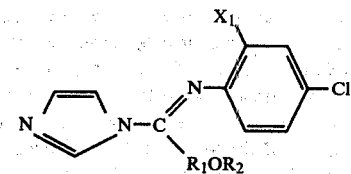

wherein
$X_1$ is chlorine or trifluoromethyl,
$R_1$ is lower alkylene of 1 to 2 carbon atoms such as methylene, methylmethylene and ethylene,
$R_2$ is lower alkyl of 2 to 4 carbon atoms or allyl
and metal complexes thereof.

The compound of the present invention can be prepared by the reaction shown as follows:

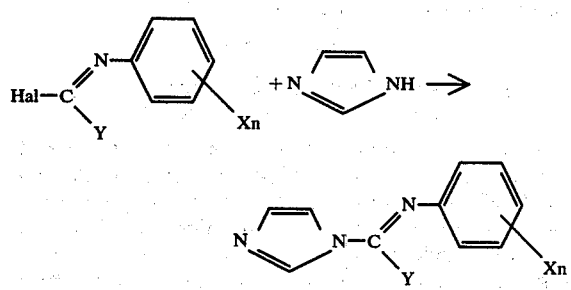

("Hal" represents halogen.)

The reaction is carried out in an inert solvent in the presence of an alkaline condensing agent such as sodium carbonate, potassium carbonate, sodium hydroxide, sodium methylalcoholate, trimethylamine, triethylamine, pyridine or piperidine. As an inert solvent, chloroform, dichloromethane, benzene, toluene, xylene, chlorobenzene, acetonitrile, acetone, dimethylsulfoxide, tetrahydrofuran, dimethylformamide or dioxane may be used. Ordinerily, a temperature from the range of 0 to the boiling point of the reaction solution, preferably a temperature from 40° C. to the boiling point, is satisfactory. The reaction is usually completed in 1 to 3 hours. After completion of the reaction, the reaction solution is washed with water and dried. The washing and drying may be carried out after replacing the solvent, if necessary. Then the solvent is distilled to obtain the desired compound.

Metal complexes of the present invention can be prepared by the following equation.

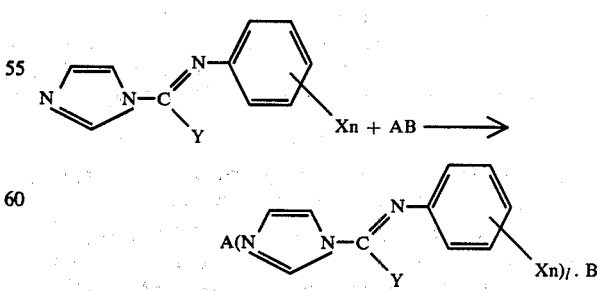

(AB is an organic or inorganic metal salt, A is bivalent or trivalent metal atom, B is anion component of the salt, and l corresponds to the valence of metal atom "A" in the metal salt "AB".

As the metal salt, chloride, sulfate, nitrate or acetate of copper, zinc, nickel, cobalt, iron or silver is used. Copper sulfate, copper chloride, zinc chloride or zinc acetate is preferably used. When carrying out the reaction for the preparation of the metal complexes, the imidazole derivative is dissolved in an inert solvent and a metal salt is added thereto and the mixture is stirred to allow to react. The reaction is ordinarily carried out at a room temperature for several minutes. As an inert solvent, any solvents which dissolve the imidazole derivative and are miscible with water can be used.

Ordinarily, ethyl acetate, methanol, acetonitrile, dioxane or tetrahydrofuran is used. After completion of the reaction, the reaction mixture is poured into n-hexane or water and the precipitated crystal is removed from it by filtration to obtain the metal complex of the present invention.

The following are examples of preparation of compound of the present invention.

EXAMPLE 1

1-[N-(2-bromophenyl)-2-ethoxypropanimidoyl]-imidazole (Compound No. 3)

11 g of 2'-bromo-2-(ethoxy)propionanilide were allowed to react with 8.4 g of phosphorus pentachloride in 50 ml of chloroform by heating the solution under reflux for 30 minutes. Then, chloroform and phosphorus oxychloride formed as by-product were removed by distillation and the residue was dissolved in 40 ml of acetonitrile. To the solution were added 2.8 g of imidazole and 4.1 g of triethylamine and then, the mixture was heated under reflux for 3 hours. After completion of the reaction, acetonitrile was distilled off and the residue was dissolved in 30 ml of dichloromethane. The solution was washed with water several times and dried over anhydrous magnesium sulfate. After distillation of dichloromethane, the residual oily product was purified by silicagel chromatography with dichloromethane to yield 4 g of the desired compound. ($n_D^{25}$ 1.5870)

EXAMPLE 2

1-[N-(2,4-dichlorophenyl)-2-propoxypropanimidoyl]-imidazole (Compound No. 9)

7.5 g of 2',4'-dichloro-2-(propoxy)propionanilide were allowed to react with 5.6 g of phosphorus pentachloride in 40 ml of chloroform by heating the solution under reflux for 30 minutes. Then, chloroform and phosphorus oxychloride formed as a by-product were removed by distillation under reduced pressure and the residue was dissolved in 40 ml of acetonitrile. To the solution were added 1.9 g of imidazole and 2.7 g of triethylamine and the mixture were heated under reflux for 3 hours. After completion of the reaction, the reaction solution was treated as in Example 1, and 4 g of the desired compound were obtained. ($n_D^{25}$ 1.5690)

EXAMPLE 3

1-[N-(4-chloro-2-trifluoromethylphenyl)-2-allyloxy-propanimidoyl] imidazole (Compound No. 11)

9.3 g of 4'-chloro-2'-trifluoromethyl-2-(allyloxy)propionanilide were allowed to react with 6.3 g of phosphorus pentachloride in 40 ml of chloroform by heating the solution under reflux for 30 minutes. Then, chloroform and phosphorus oxychloride were removed by distillation and the residue was dissolved in 40 ml of acetonitrile. To the solution were added 2.1 g of imidazole and 3 g of triethylamine and then, the mixture was heated under reflux for 3 hours. After completion of the reaction the reaction solution was treated as in Example 1, and 5 g of the desired compound were obtained. ($n_D^{22}$ 1.5440)

EXAMPLE 4

1-[N-(2,4-dichlorophenyl)-2-butoxypropanimidoyl]-imidazole (Compound No. 19)

8.8 g of 2',4'-dichloro-2-(butoxy)propionanilide were allowed to react with 6.4 g of phosphorus pentachloride in 40 ml of chloroform by heating the solution under reflux for 30 minutes. Then, chloroform and phosphorus oxychloride were removed by distillation and the residue was dissolved in 40 ml of acetonitrile. To the solution were added 2.1 g of imidazole and 3 g of triethylamine and then, the mixture was heated under reflux for 3 hours. After completion of the reaction, the same treatment as in Example 1 was carried out to yield 4.5 g of the desired compound ($n_D^{25.5}$ 1.5682)

EXAMPLE 5

1-[N-(2,4-dichlorophenyl)-3-propoxypropanimidoyl]-imidazole (Compound No. 36)

6.9 g of 2',4'-dichloro-3-(propoxy)propionanilide and 8 g of triethylamine were dissolved in 30 ml of chloroform and 3.7 g of phosgene were introduced thereto at 0° to 10° C. under cooling with ice. After raising the temperature of the solution to room temperature, the solution was stirred for 2 hours, and then, 2 g of imidazole were added thereto. The mixture was heated under reflux for 2 hours. After completion of the reaction, the resulting reaction solution was cooled to room temperature, washed with water and dried over anhydrous magnesium sulfate. Removal of chloroform from the solution by distillation gave 7.7 g of the desired compound. ($n_D^{29}$ 1.5688)

EXAMPLE 6

1-[N-(4-chlor-2-trifluoromethylphenyl)-2-propoxyacetimidoyl]-imidazole (Compound No. 37)

12.6 g of 4'-chloro-2'-trifluoromethyl-2-(propoxy)acetanilide and 12.9 g of triethylamine were dissolved in 80 ml of chloroform, and the solution of 6.4 g of phosgene in 30 ml of chloroform was added dropwise thereto.

The solution was stirred for one hour at room temperature, and then, after adding 4.4 g of imidazole thereto, the mixture was stirred for 15 hours at room temperature. After completion of the reaction, chloroform was removed by distillation. The resulting residue was dissolved in n-hexane, and the solution was washed with water and dried over anhydrous magnesium sulfate. After removal of n-hexane by distillation, the residue was purified by silicagel chromatography to yield 9.8 g of the desired compound. ($n_D^{23.5}$ 1.5370)

EXAMPLE 7

1-[N-(4-chloro-2-trifluoromethylphenyl)-sec-butoxyacetimidoyl] imidazole (Compound No. 39)

7 g of 4'-chloro-2'-trifluoromethyl-sec-butoxyacetanilide were allowed to react with 5.2 g of phosphorus pentachloride in 50 ml of benzene by heating the solution under reflux for one hour. Then, benzene and phosphorus oxychloride were removed by distillation under reduced pressure and the residual oily product was dissolved in 50 ml of chloroform. To the solution were added 1.7 g of imidazole and triethylamine and then, the mixture was heated for one hour at 50° C. with stirring.

After completion of the reaction, the solution was washed with water and dried and chloroform was removed by distillation. The residue was purified by silicagel chromatography to yield 1.85 g of the desired compound. ($n_D^{21}$ 1.5378)

EXAMPLE 8

1-[N-(4-chloro-2-trifluoromethylphenyl)-2-ethoxyacetimidoyl]-imidazole (Compound No. 40)

10 g of 4'-chloro-2'-trifluoromethyl-2-(ethoxy)acetanilide and 10.8 g of triethylamine were dissolved in 80 ml of chloroform, and the solution of 5.3 g of phosgene in 30 ml of chloroform was added dropwise thereto.

After stirring the solution for one hour at room temperature, 2.9 g of imidazole were added thereto and the mixture was stirred for 15 hours at room temperature. After completion of the reaction, chloroform was removed by distillation and the residue was dissolved in n-hexane. The solution was washed with water and dried over anhydrous magnesium sulfate. Removal of n-hexane from the solution by distillation gave 10.2 g of the desired compound. (m.p. 49°–52° C.)

EXAMPLE 9

1-[N-(2,4-dichlorophenyl)-4-chloro-2-methylphenoxyacetimidoyl]imidazole (Compound No. 43)

3.4 g of 2',4'-dichloro-(4-chloro-2-methylphenoxy)acetanilide were allowed to react with 2.3 g of phosphorus pentachloride in 40 ml of benzene by heating the solution under reflux for one hour. Then, benzene and phosphorus oxychloride were removed by distillation under reduced pressure and the residual oily product was dissolved in 40 ml of chloroform. To the solution were added 0.75 of imidazole and 1.1 g of triethylamine and the mixture was stirred for one hour at 50° C. After completion of the reaction, the same treatment as in Example 7 was carried out to yield 1.1 g of crystal of the desired compound. (m.p. 84°–86° C.)

EXAMPLE 10

1-[N-(4-chloro-2-trifluoromethylphenyl)-3-ethoxypropanimidoyl]imidazole (Compound No. 46)

6.5 g of 4'-chloro-2'-trifluoromethyl-2-(ethoxy)propionanilide were allowed to react with 4.9 g of phosphorus pentachloride in 30 ml of chloroform under reflux for one hour. Then, chloroform and phosphorus oxychloride were removed by distillation under reduced pressure. To the residue were added 3.2 g of imidazole and 30 ml of acetonitrile, and the mixture was heated for 30 minutes under reflux. After completion of the reaction, acetonitrile was removed by distillation and the residue was dissolved in dichloromethane. The solution was washed with water and dried over anhydrous magnesium sulfate. After removal of the solvent from the solution by distillation, the residue was purified by alumina column chromatography to yield 3.5 g of the desired compound. (m.p. 61°–2° C.)

EXAMPLE 11

Bis[1-{N-(2,4-dichlorophenyl)-2-propoxypropanimidoyl}-imidazole]copper chloride (Compound No. 56)

1 g of 1-{N-(2,4-dichlorophenyl)-2-propoxypropanimidoyl}-imidazole was dissolved in 5 ml of methanol and 0.5 g of anhydrous copper chloride were added thereto. The mixture was stirred for 5 minutes at room temperature and then, poured into 100 ml of water to precipitate crystal. Separated crystal by filtration was washed with water and then with n-hexane. The crystal was dried under reduced pressure to yield 1 g of the desired complex. (m.p. 165°–169° C.).

EXAMPLE 12

Bis[1-{N-2,4-dichlorophenyl)-2-propoxypropanimidoyl}-imidazole]zinc chloride (Compound No. 57)

The reaction of 2 g of 1-[N-(2,4-dichlorophenyl)-2-propoxypropanimidoyl]-imidazole with 0.5 g of anhydrous zinc chloride was carried out as in Example 11 to give 2 g of the desired complex. (m.p. 157°–158° C.)

Examples of compounds of the present invention are listed in Tables 1 and 2.

Table 1

| Compound No. | Xn | Y | Physical Constant [m.p.] °C. |
|---|---|---|---|
| 1 | 2-F | —CH(CH$_3$)—O—C$_2$H$_5$ | $n_D^{23.5}$ 1.5585 |
| 2 | 2-Br | —CH(CH$_3$)—O—C$_6$H$_5$ | $n_D^{26}$ 1.6222 |
| 3 | " | —CH(CH$_3$)—O—C$_2$H$_5$ | $n_D^{25}$ 1.5870 |
| 4 | 2,4-Cl$_2$ | —CH(C$_3$H$_7^n$)—O—CH$_3$ | $n_D^{24}$ 1.5800 |
| 5 | " | —CH(CH$_3$)—O—C$_2$H$_5$ | $n_D^{24}$ 1.5833 |
| 6 | 2-CF$_3$-4-Cl | —CH(C$_3$H$_7^n$)—O—CH$_3$ | $n_D^{24}$ 1.5430 |
| 7 | " | —CH(CH$_3$)—O—C$_2$H$_5$ | $n_D^{24}$ 1.5340 |
| 8 | 2,4-Br$_2$ | " | $n_D^{25}$ 1.6090 |
| 9 | 2,4-Cl$_2$ | —CH(CH$_3$)—O—C$_3$H$_7^n$ | $n_D^{25}$ 1.5690 |
| 10 | " | —CH(CH$_3$)—O—CH$_2$CH=CH$_2$ | $n_D^{25}$ 1.5705 |
| 11 | 2-CF$_3$-4-Cl | " | $n_D^{22}$ 1.5440 |
| 12 | 2-CH$_3$ | —CH(CH$_3$)—O—C$_2$H$_5$ | $n_D^{22}$ 1.5620 |
| 13 | 2-NO$_2$ | " | [73–76] |
| 14 | 2-CF$_3$ | " | $n_D^{23.5}$ 1.5292 |
| 15 | 2-Br-4-NO$_2$ | " | [160–161] |
| 16 | 2-Cl | " | $n_D^{25.5}$ 1.5720 |
| 17 | 2-CF$_3$-4-Cl | —CH(CH$_3$)—O—C$_3$H$_7$n | $n_D^{25.5}$ 1.5300 |
| 18 | 2-Br | " | $n_D^{25.5}$ 1.5820 |
| 19 | 2,4-Cl$_2$ | —CH(CH$_3$)—O—C$_4$H$_9^n$ | $n_D^{25.5}$ 1.5682 |
| 20 | 2-CF$_3$-4-Cl | " | $n_D^{25.5}$ 1.5295 |

Table 1-continued

| Compound No. | Xn | Y | Physical Constant [m.p.] °C. |
|---|---|---|---|
| 21 | 2-Cl-5-$CH_3$ | $-CH(CH_3)-O-C_2H_5$ | $n_D^{25}$ 1.5668 |
| 22 | 2,4-Cl | $-CH(CH_3)-O-C_3H_7^i$ | $n_D^{27.5}$ 1.5700 |
| 23 | 2-$CF_3$-4-Cl | " | [86–87] |
| 24 | 2,4-$Cl_2$ | $-CH(CH_3)-O-C_4H_9^i$ | $n_D^{27.5}$ 1.5684 |
| 25 | 2-$CF_3$-4-Cl | " | $n_D^{27.5}$ 1.5275 |
| 26 | 3,4-$Cl_2$ | $-CH(CH_3)-O-C_2H_5$ | $n_D^{28}$ 1.5782 |
| 27 | 2-$C_2H_5$ | " | $n_D^{27}$ 1.5541 |
| 28 | 2-$NO_2$-4-Cl | " | $n_D^{27}$ 1.5959 |
| 29 | 2-$NO_2$-6-$CH_3$ | " | $n_D^{27}$ 1.5799 |
| 30 | 4-Cl | $-CH(CH_3)-O-C_4H_9^n$ | $n_D^{29}$ 1.5690 |
| 31 | 2-Cl | $-CH(CH_3)-O-C_3H_7^n$ | $n_D^{31.5}$ 1.5650 |
| 32 | 2,4-$Cl_2$ | $-CH(CH_3)-O-$phenyl | $n_D^{24}$ 1.6171 |
| 33 | 2-$CF_3$-4-Cl | " | [90–93] |
| 34 | " | $-CH(CH_3)-O-CH(CH_3)C_2H_5$ | $n_D^{29}$ 1.5382 |
| 35 | 2,4-$Cl_2$ | " | $n_D^{26}$ 1.5692 |
| 36 | 2,4-$Cl_2$ | $-(CH_2)_2-O-C_3H_7^n$ | $n_D^{29}$ 1.5688 |
| 37 | 2-$CF_3$-4-Cl | $-CH_2-O-C_3H_7^n$ | $n_D^{23.5}$ 1.5370 |
| 38 | 2,4-$Cl_2$ | " | $n_D^{27}$ 1.5765 |
| 39 | 2-$CF_3$-4-Cl | $-CH_2-O-CH(CH_3)C_2H_5$ | $n_D^{34}$ 1.5292 |
| 40 | " | $-CH_2-O-C_2H_5$ | [49–52] |
| 41 | 2,4-$Cl_2$ | " | $n_D^{21}$ 1.5962 |
| 42 | 2-$CF_3$-4-Cl | $-CH_2-O-(2-CH_3-4-Cl\text{-phenyl})$ | $n_D^{20}$ 1.5875 |
| 43 | 2,4-$Cl_2$ | " | [84–86] |
| 44 | " | $-(CH_2)_2-O-C_2H_5$ | $n_D^{20}$ 1.5952 |
| 45 | 2-$CF_3$-4-Cl | $-(CH_2)_2-O-C_3H_7^n$ | $n_D^{21}$ 1.5463 |
| 46 | " | $-(CH_2)_2-O-C_2H_5$ | [61–62] |
| 47 | " | $-CH_2-O-C_4H_9^n$ | $n_D^{23}$ 1.5396 |
| 48 | " | $-CH_2-O-CH(CH_3)-C_3H_7$ | $n_D^{22}$ 1.5295 |
| 49 | 2,4-$Cl_2$ | " | $n_D^{22}$ 1.5705 |
| 50 | " | $-CH_2-O-C_4H_9^n$ | $n_D^{22.5}$ 1.5765 |
| 51 | 2-$CF_3$-4-Cl | $-CH_2-O-C_5H_{11}^n$ | $n_D^{22.5}$ 1.5300 |
| 52 | 2,4-$Cl_2$ | " | $n_D^{22.5}$ 1.5717 |
| 53 | 2-$CF_3$-4-Cl | $-CH_2-O-C_3H_7^i$ | $n_D^{22.5}$ 1.5363 |
| 54 | 2,4-$Cl_2$ | " | [52–53] |
| 55 | 2-$CF_3$-4-Cl | $-CH_2-O-C_8H_{17}^n$ | $n_D^{24}$ 1.5225 |

Table 2

| Compound No. | Xn | Y | AB | Physical Constant [m.p.] °C. |
|---|---|---|---|---|
| 56 | 2,4-$Cl_2$ | $-CH(CH_3)-O-C_3H_7^n$ | $CuCl_2$ | [165–169] |
| 57 | " | " | $ZnCl_2$ | [157–158] |
| 58 | " | " | $CuSO_4$ | [90–94] |
| 59 | 2-$CF_3$-4-Cl | " | $ZnCl_2$ | [48–53] |
| 60 | " | $-CH(CH_3)-O-C_2H_5$ | " | [71–75] |
| 61 | " | $-CH_2-O-C_2H_5$ | " | [52–56] |
| 62 | " | " | $CuSO_4$ | [91–94] |
| 63 | " | $-(CH_2)_2-O-C_2H_5$ | " | [138–141] |
| 64 | 2-$CF_3$-4-Cl | $-CH_2-O-C_4H_9^n$ | $ZnCl_2$ | [58–64] |
| 65 | " | $-CH_2-O-C_3H_7^n$ | $CuSO_4$ | [77–81] |
| 66 | " | " | $ZnCl_2$ | [71–74] |
| 67 | " | $-CH(CH_3)-O-CH(CH_3)C_2H_5$ | $CuSO_4$ | [76–78] |
| 68 | " | " | $ZnCl_2$ | [64–66] |
| 69 | 2,4-$Cl_2$ | $-CH_2-O-C_4H_9^n$ | $CuSO_4$ | [117–120] |
| 70 | " | $-CH_2-O-C_5H_{11}^n$ | " | [103–108] |
| 71 | 2-$CF_3$-4-Cl | $-CH_2-O-C_3H_7^i$ | " | [81–86] |
| 72 | 2,4-$Cl_2$ | " | " | [132–136] |
| 73 | 2-$CF_3$-4-Cl | $-CH_2-O-C_5H_{11}^n$ | " | [144–151] |
| 74 | " | " | $ZnCl_2$ | [55–64] |
| 75 | " | $-CH_2-O-C_3H_7^i$ | " | [83–88] |

Table 2-continued $$A(N \diagup\diagdown N-C(\diagdown Y)(=N-C_6H_{4-}Xn)_{l} \cdot B^*$$

| Compound No. | Xn | Y | AB | Physical Constant [m.p.] °C. |
|---|---|---|---|---|
| 76 | 2,4-Cl$_2$ | —CH$_2$—O . CH(CH$_3$)—C$_3$H$_7^n$ | CuSO$_4$ | [78–80] |
| 77 | 2-CF$_3$-4-Cl | " | " | [74–76] |
| 78 | 2,4-Cl | —CH(CH$_3$)—O—C$_3$H$_7^n$ | FeCl$_3$ | [50–56] |
| 79 | " | " | Cu(CH$_3$COO)$_2$ | [138–141] |
| 80 | " | " | Zn(CH$_3$COO)$_2$ | [128–130] |

"l" corresponds to the valence of metal atom "A" in the metal salt "AB".

In the Tables 1 and 2, preferable compounds as fungicides are Compound Nos. 9, 11, 17, 22, 23, 34, 36, 37, 38, 39, 40 and metal complexes thereof such as Compound Nos. 56, 57, 58, 61 and 62.

Most of the metal complexes have superior fungicidal activity and superior risidual activity to the corresponding free imidazole derivatives.

As mentioned previously, it has been found that compounds of the present invention possess fungicidal activity when employed to prevent damage to plants.

Such compounds may control a wide variety of fungus diseases of foliage, fruit, stems and roots of growing plants, without damage to the host.

The many fungi against which such compounds are active may be represented by, but is not intended to be limited to, the following:

gray mold, sclerotia rot, damping-off and powdery mildew of vegetables, brown rot of peach, leaf spot of corn, scab of apples and pear, rust of pear, powdery mildew of apple, and rust of cereals; and the compounds are particularly effective against powdery mildew, scab and rust.

It is another advantage that such compounds cause no phyto-toxicity to plants.

The method of the present invention includes the employment of a liquid or solid composition containing one or more of the compounds as an active component.

The compound may be used directly without mixing with suitable carrier.

The active ingredient of a fungicidal composition exemplifying the invention may be formulated by mixing with suitable carriers in a form generally used in pesticidal compositions, such as wettable powder, emulsifiable concentrate, dust formulation, granular formulation, water soluble powder and aerosol. As solid carriers, bentonite, diatomaceous earth, apatite, gypsum, talc, pyrophyllite, vermiculite and clay, for example, may be used. As liquid carriers, kerosene, mineral oil, petroleum, solvent naphtha, xylene, cyclohexane, cyclohexanone, dimethylformamide, dimethylsulfoxide, alcohol, acetone benzene and water, for example, may be used. If so desired, a surface active agent may be added in order to give a homogeneous and stable formulation.

Further, in the case of using metal complexes of the present invention as active ingredients, the mixture of corresponding free imidazole derivative and metal salt may be used instead of the metal complex. Namely, the free imidazole derivative and metal salt such as zinc chloride, copper chloride or copper sulfate may be mixed when formulating the fungicidal composition, or when applying to plants. Furthermore, metal containing pesticides such as mancozeb, oxine-copper or fentin hydroxide may be mixed with the imidazole derivatives same as the above-mentioned metal salt.

The concentration of the active ingredient in the fungicidal composition may vary according to type of formulation, and is for example, 5 to 80 weight percent, preferably 20 to 80 weight percent, in wettable powders; 5 to 70 weight percent, preferably 10 to 50 weight percent, in emulsifiable concentrates; and 0.5 to 20 weight percent, preferably 1 to 10 weight percent, in dust formulations.

A wettable powder or an emulsifiable concentrate containing a quantity of the active compound may be suspended or emulsified in water and then sprayed on the foliage of plants or on the locus to be protected.

Furthermore, the compounds may be used in mixture with other fungicides, insecticides, acaricides and herbicides.

Some non-limiting examples of fungicidal compositions according to the invention are as follows:

EXAMPLE 13

| | Parts by weight |
|---|---|
| Compound No. 9 | 40 |
| Diatomaceous earth | 53 |
| Higher alkyl sulfate | 4 |
| Alkylnaphthalene sulfonic acid | 3 |

These are mixed homogeneously and reduced to fine particles to provide a wettable powder containing 40% of the active ingredient. In use, the powder is diluted to a desired concentration with water and is sprayed as a suspension.

EXAMPLE 14

Emulsifiable Concentrate

| | Parts by weight |
|---|---|
| Compound No. 11 | 30 |
| Xylene | 33 |
| Dimethylformamide | 30 |
| Polyoxyethylene alkylallylether | 7 |

These are mixed and dissolved to provide an emulsifiable concentrate containing 30% of the active ingredient. In use, the concentrate is diluted to a desired concentration with water and then is sprayed as an emulsion.

EXAMPLE 15

Dust Formulation

|  | Parts by weight |
|---|---|
| Compound No. 61 | 10 |
| Talc | 89 |
| Polyoxyethylene akylallyether | 1 |

These are mixed homogeneously and reduced to fine particles to provide a dust formulation containing 10% of the active ingredient. In use, the formulation is applied directly.

The fungicidal activity of compounds of this invention is illustrated by the following tests:

Test 1. Test for Control of Gray Mold of Bean

The detached leaves of kidney beans (*Phaseolus vulgaris*) were immersed for about 30 seconds in an aqueous suspension prepared by diluting a wettable powder to a concentration of 200 ppm of a test compound. After air-dried, the treated leaves were inoculated with mycelia of *Botrytis cinerea* and kept at 20° C. in a moist chamber. Control effect was checked 4 days after inoculation. The results are shown in Table 3.

Test 2. Test for Control of Cucumber Powdery Mildew

The leaves of potted cucumber seedlings (variety: Satsukimidori) at 1–2 leaf stage were sprayed with an aqueous suspension (5 ml/pot) prepared by diluting a wettable powder to a concentration of 100 ppm of a test compound. After air-dried, the treated leaves were inoculated with conidia of *Sphaerotheca fuliginea* and kept for 9 days at 25° C. in a greenhouse. Then, control effect was checked. The results are shown in Table 3.

Test 3. Test for Control of Rhizoctonia Damping-off of Cucumber

Cucumber seedlings (variety: Suyo) at the cotyledon stage were treated by injecting an aqueous suspension containing a test compound at 100 ppm into the soil (10 ml/pot with 7 seedlings) after inoculated with mycelia of *Rhizoctonia solani*. Control effect was evaluated 4 days after inoculation. The results are shown in Table 3.

Table 3

| Compound No. | Control Value (%) | | |
|---|---|---|---|
| | Test 1 | Test 2 | Test 3 |
| 1 | 99 | | |
| 2 | | 93 | 84 |
| 3 | 100 | 97 | 100 |
| 4 | 100 | 100 | |
| 5 | 100 | 100 | |
| 6 | 100 | 100 | |
| 7 | 100 | 100 | 100 |
| 8 | 100 | 100 | |
| 9 | 100 | 100 | 100 |
| 10 | 100 | 95 | |
| 11 | 100 | 100 | 100 |
| 12 | 100 | 95 | |
| 13 | 100 | | 89 |
| 14 | 100 | 100 | 100 |
| 15 | 100 | 95 | |
| 16 | 100 | 95 | 100 |
| 17 | 100 | 100 | 100 |
| 18 | 100 | 100 | 100 |
| 19 | 100 | 95 | 100 |
| 20 | 100 | 100 | 100 |
| 21 | 100 | 100 | 86 |
| 22 | 100 | 100 | 100 |
| 23 | 100 | 100 | 100 |
| 24 | 100 | 100 | 86 |
| 25 | 100 | 100 | 100 |
| 26 | 100 | | |
| 27 | 100 | 100 | 95 |
| 28 | 100 | | 89 |
| 29 | 100 | | 100 |
| 30 | 100 | | 87 |
| 36 | | 95 | |
| 37 | 93 | 100 | 100 |
| 38 | 95 | 100 | 100 |
| 39 | 100 | 100 | 100 |
| 40 | 95 | 100 | 100 |
| 41 | | 100 | 79 |
| 42 | | 90 | 86 |
| 43 | | 95 | 100 |
| 45 | 100 | 100 | |
| 46 | 100 | 100 | |
| 56 | 100 | 100 | 100 |
| 57 | 100 | 100 | 100 |
| 58 | 100 | 100 | 100 |
| 59 | 100 | 100 | 100 |
| 60 | 100 | 100 | 100 |
| 61 | 100 | 100 | 100 |
| 62 | 100 | 100 | 100 |
| 63 | 100 | 100 | |
| Comparative compound* | | | |
| 1 | | 63 | 0** |
| 2 | 90 | | |
| 3 | | 90 | |
| 4 | | | 90 |
| untreated | 0 | 0 | 0 |

*Comparative compound

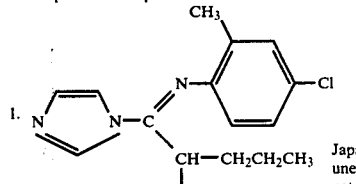

1. Japanese published unexamined patent application No. 39674/77
2. Euparen: N'-dichlorofluoromethylthio-N,N-dimethyl-N'-phenylsulfamide
3. Morestan: 6-methyl-1,3-dithiolo[4,5-b]quinoxaline-2-one
4. PCNB: Pentachloronitrobenzene

**Phyto-toxicity was observed.

We claim:

1. A compound selected from the group consisting of (a) an imidazole compound of the general formula

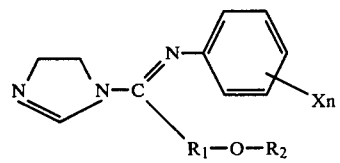

wherein

X is the same or a different substituent selected from the ground consisting of halogen, methyl, nitro and trifluoromethyl;

n is one or two;

$R_1$ is alkylene having 1 to 4 carbon atoms;

$R_2$ is alkyl having 1 to 8 carbon atoms, allyl, phenyl or phenyl substituted with methyl and chlorine; and (b) a metal complex of the imidazole compound in (a) with a metal salt of the formula AB selected from the group consisting of $CuCl_2$, $CuSO_4$, $Cu(CH_3COO)_2$, $ZnCl_2$, $Zn(CH_3COO)$, and $FeCl_3$, said metal complex represented by the formula

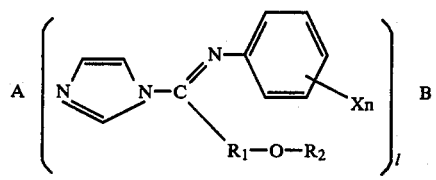

wherein l is 2 or 3, corresponding to the valence of metal atom A in the metal salt AB.

2. A compound according to claim 1, sections (a) and (b) wherein the imidazole compound is represented by the formula

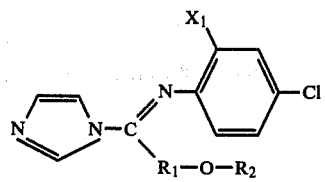

$X_1$ being trifluoromethyl or chlorine.

3. A compound according to claim 2, wherein $R_1$ is lower alkylene of 1 to 2 carbon atoms and $R_2$ is lower alkyl of 2 to 4 carbon atoms or allyl.

4. A fungicidal composition, comprising an inert carrier and a fungicidally effective amount of a compound of claim 1 sections (a) and (b).

5. A fungicidal composition, comprising an inert carrier and a fungicidally effective amount of a compound of claim 2.

6. A fungicidal composition, comprising an inert carrier and a fungicidally effective amount of a compound of claim 3.

7. A method for the control of fungi, comprising applying to the locus to be protected an effective amount of a compound of claim 1.

8. A method for the control of fungi, comprising applying to the locus to be protected an effective amount of a compound of claim 2.

9. A method for the control of fungi, comprising applying to the locus to be protected an effective amount of a compound of claim 3.

* * * * *